(12) United States Patent
Kaupp et al.

(10) Patent No.: US 7,651,562 B2
(45) Date of Patent: Jan. 26, 2010

(54) PIGMENT AND PIGMENTED COSMETIC PREPARATION AS WELL AS METHOD FOR PRODUCTION OF THE PIGMENT

(75) Inventors: Gunter Kaupp, Neuhaus (DE); Thomas Schuster, Lauf (DE); Hans-Jorg Kremitzl, Eckental (DE); Gunter Sommer, Hersbruck (DE)

(73) Assignee: Eckart GmbH & Co. KG, Furth (DE)

( * ) Notice: Subject to any disclaimer, the term of this patent is extended or adjusted under 35 U.S.C. 154(b) by 89 days.

(21) Appl. No.: 10/525,395

(22) PCT Filed: Aug. 7, 2003

(86) PCT No.: PCT/EP03/08729

§ 371 (c)(1),
(2), (4) Date: Feb. 22, 2005

(87) PCT Pub. No.: WO2004/026268

PCT Pub. Date: Apr. 1, 2004

(65) Prior Publication Data

US 2006/0032403 A1   Feb. 16, 2006

(30) Foreign Application Priority Data

Aug. 21, 2002 (DE) ................................. 102 38 090

(51) Int. Cl.
   C04B 14/00 (2006.01)
   C09C 1/62 (2006.01)
   B32B 5/16 (2006.01)
(52) U.S. Cl. .................. 106/400; 106/404; 428/403
(58) Field of Classification Search ................. 106/403, 106/404, 480, 499, 286.7, 400, 415, 435; 428/403, 404
See application file for complete search history.

(56) References Cited

U.S. PATENT DOCUMENTS

| | | | | |
|---|---|---|---|---|
| 3,389,105 A | * | 6/1968 | Bolger | 523/205 |
| 3,389,116 A | * | 6/1968 | Saha | 106/404 |
| 4,978,394 A | | 12/1990 | Ostertag et al. | |
| 5,037,475 A | * | 8/1991 | Chida et al. | 106/403 |
| 5,143,723 A | * | 9/1992 | Calvo et al. | 424/63 |
| 5,213,618 A | * | 5/1993 | Souma et al. | 106/403 |
| 5,318,628 A | * | 6/1994 | Matijevic et al. | 106/499 |
| 5,607,504 A | * | 3/1997 | Schmid et al. | 106/403 |
| 5,702,518 A | * | 12/1997 | Vogt et al. | 106/439 |
| 5,718,753 A | * | 2/1998 | Suzuki et al. | 106/403 |
| 5,849,817 A | * | 12/1998 | Green et al. | 523/515 |
| 5,931,996 A | * | 8/1999 | Reisser et al. | 106/404 |
| 6,030,627 A | | 2/2000 | Seo et al. | |
| 6,398,861 B1 | | 6/2002 | Knox | |
| 6,596,071 B2 | * | 7/2003 | Hayashi et al. | 106/445 |
| 2002/0134282 A1 | | 9/2002 | Ostertag et al. | |
| 2002/0169244 A1 | | 11/2002 | Ostertag et al. | |
| 2003/0209169 A1 | * | 11/2003 | Andes et al. | 106/415 |
| 2004/0180010 A1 | | 9/2004 | Andes et al. | |

FOREIGN PATENT DOCUMENTS

| | | |
|---|---|---|
| DE | 4437753 A1 | 4/1996 |
| DE | 198 36 810 A1 | 2/2000 |
| DE | 19836810 A1 | 2/2000 |
| DE | 101 14 446 A1 | 9/2002 |
| DE | 10114445 A1 | 9/2002 |
| EP | 0 338 428 A1 | 10/1989 |
| EP | 0338428 A1 | 10/1989 |
| EP | 0665004 A2 | 8/1995 |
| EP | 0665004 A3 | 8/1995 |
| EP | 0 673 980 A2 | 9/1995 |
| JP | 01-311176 A | 12/1989 |
| JP | 04-069317 A | 3/1992 |
| JP | 05-508424 A | 11/1993 |
| JP | 07-133211 A | 5/1995 |
| JP | 08-40830 A | 2/1996 |
| JP | 08-209024 A | 8/1996 |
| JP | 09-227114 A | 9/1997 |
| JP | 10-513206 A | 12/1998 |
| JP | 2000-044450 A | 2/2000 |
| JP | 2002-522618 A | 7/2002 |
| WO | 9104293 A1 | 4/1991 |
| WO | WO 91/04293 | 4/1991 |
| WO | 95/14732 A2 | 6/1995 |
| WO | WO 95/14732 * | 6/1995 |
| WO | WO 00/09617 * | 2/2000 |

OTHER PUBLICATIONS

"Pigments for high performance" Additives for polymers, Jul. 1998, pp. 10-11.*
Database WPI, Section Ch, Week 199801, Derwent Publications Ltd., London, GB, An 1998-002739, XP002265350 & JP 09 227114 A (Mori S), Sep. 2, 1998, abstract, pp. 1-2.
European Search Report dated Feb. 14, 2008.
Japanese Office Action dated Dec. 11, 2007.

* cited by examiner

Primary Examiner—Jerry Lorengo
Assistant Examiner—Shuangyi Abu Ali
(74) Attorney, Agent, or Firm—Browdy and Neimark, PLLC

(57) ABSTRACT

In a metal pigment for a cosmetic preparation, such as lipstick, nail polish, eye shadow, hair colorant, liquid mascara, powder, eyeliner, rouge, skin/hair care products, perfume, eau de toilette, lotions or the like, provision is made for a metallic substrate to have a substrate-enclosing layer produced by the sol-gel process, which provides a barrier effect against sweat and saliva and prevents direct contact between skin and metallic substrate.

18 Claims, No Drawings

PIGMENT AND PIGMENTED COSMETIC PREPARATION AS WELL AS METHOD FOR PRODUCTION OF THE PIGMENT

The invention relates to a pigment for a cosmetic preparation, such as lipstick, nail polish, eye shadow, hair colorant, liquid mascara, liquid self-tanner or the like and to a cosmetic preparation containing such a pigment.

Cosmetic preparations of the type in question, such as loose or pressed powders, eye shadows, lipsticks, eyeliners, nail polishes, rouges, mascaras or the like, are composed of a carrier material or a base formulation as well as color-imparting and effect-imparting means of various types, with the goal to obtain a certain color effect on the skin, lips or hair.

These color-imparting and effect-imparting means may be colorants, lacquered organic colorants, inorganic or organic pigments or effect pigments, wherein especially in case of the effect pigments, special emphasis lies on the desire to attain a different color impression or brightness impression depending on the viewing angle of the applied preparation. To achieve this purpose, pearlescent pigments in particular have conventionally been used in the field of cosmetics.

Pearlescent pigments are based on flake-shaped mica particles as a substrate, which are coated with metal oxides, mainly with titanium dioxide or iron oxide. Pigments of this type on the basis of titanium oxide, however, are relatively transparent due to their composition and, as a rule, exhibit a color impression only at the so-called "glancing angle", whereas pigments that are based on iron oxide provide more coverage but the angle-dependent color impression or brightness impression is pushed into the background. The advantage of these pigments lies in their high chemical and thermal stability that virtually preclude negative effects for example on a binding agent, as well as in their skin tolerance.

So far as metal effect pigments have been used for cosmetic purposes until now, it is true that they have the advantage that they are covering, color-intensive and highly brilliant, however they have the shortcoming, in particular, that they to not meet the health requirements, considering especially that metal ions from the metal component, for example copper or zinc ions, are released into the carrier medium and cause undesired effects, such as gelling of binding agents and color changes. In the applied condition, contact with sweat or saliva may occur, which means with acidic or basic media, which can also cause an increased release of ions that not only affect the carrier substance but may possibly result directly in health-related damage, such a skin irritations.

From DE 44 37 753 A1 a lustrous pigment is known that is also usable for cosmetic purposes, which consists of at least five layers and is accordingly expensive to produce.

DE 198 36 810 A1 describes metal pigments that are coated in an aqueous medium, which is associated with the shortcomings that will be described below.

DE 101 14 445 A1 and DE 101 14 446 A1 describe iron pigments that are not approved for cosmetic applications. The same applies for the iron pigment according to EP 0 673 980 A2, which is treated at a raised temperature in an oxygen atmosphere.

U.S. Pat. No. 6,398,861 B1 describes a metal pigment composition, not a metal pigment as such. Reference is made to an aqueous system, and the use of tensides is mentioned, which are completely unsuitable for the inventive solution that will be described below.

Based on this, the invention is based on the object to further develop a pigment of the above type in such a way that it better meets the hygienic and health requirements than pigments that are conventionally used in the field of cosmetics.

This object is met according to the invention in such a way that a metallic substrate comprises a substrate-enclosing layer, which is produced in the sol-gel process, incorporates a barrier effect with respect to sweat and saliva, and prevents direct contact between the skin and the metallic substrate.

The sol-gel process that is provided according to the invention significantly influences the property of the substrate-encapsulating layer. In such a sol-gel process, a barrier layer is built up around the metallic substrate in organic solution or suspension from suitable monomeric metal-oxide pre-stages, e.g., alkoxy silanes, with the use of suitable catalysts. Compared to coating methods from aqueous solutions, e.g., with water glass, this process offers the advantage that no additional pretreatment is required to activate or degrease the base pigment, which is coated with auxiliary grinding agents, and the obtained layer cannot be contaminated through additional ions, such as e.g., chlorides or sulfates. Additionally, a layer that is obtained in this manner, since it was obtained from monomeric pre-stages, offers the advantage of a particularly even, dense and therefore high-quality, optically not perceptible layer, which is additionally also harmless from health-related and hygienic points of view as they are relevant particularly for the cosmetic application.

A metal pigment that has been improved in this manner does not exhibit any, or only a significantly reduced, agglomeration tendency or flocculation tendency as compared to an uncoated metal pigment or one that has been coated in the aqueous system. The optical properties are not impacted by the surrounding layer, or only to a small degree. The same applies for the haptic properties.

The layer is preferably compatible with a binding agent of a cosmetic preparation.

The layer may contain an inorganic material on one hand, or be composed of it, which will preferably be selected from the group consisting of silicon oxide, titanium oxide, aluminum oxide, iron oxide, ceroxide and chromium oxide, as well as mixtures thereof.

On the other hand, or alternatively, the layer may contain organic material or consist of it, which will expediently be selected form the group consisting of polyacrylates, silicones, polyolefins, polystyrol, polyesters, cellulose ester, polyamides, phosphor organic substances, organically modified silanes, organically modified titanates, organically modified zirconates, as well as mixtures thereof.

The thickness of the layer may be between 5 and 500 nm, especially between 20 and 50 nm.

The metallic core preferably consists of copper, zinc, aluminum, titanium, silver or gold, or alloys of said elements.

A preferred embodiment provides for the metallic core to consist of aluminum, 100% of the grain size to be <75 µm and 95%<45 µm, and the mercury content to be ≦1 ppm, arsenic ≦3 ppm, lead ≦20 ppm and the Al content ≧99%.

Provision may be made for the metallic core to consist of aluminum, the content of mercury to be <=1 ppm, of arsenic <=3 ppm, of lead <=10 ppm, of cadmium <=1 ppm, of heavy metals (as lead) <=40 ppm, the drying loss at 105° C. to be <=0.5%, and the Al content >=99%.

A bronze pigment may be characterized in the context of the invention in that the metallic core contains a copper content of 70 to 95%, a zinc content of ≦30% and an aluminum and tin content of ≦0.5% in each case, and that the content of cadmium is <=15 ppm, of lead <=20 ppm, of arsenic <=3 ppm and of mercury <=1 ppm, and 95% of the grain size is <45 µm.

In the case of a copper pigment, provision is preferably made for the metallic core to have a copper content of >=95% and the content of cadmium to be <=15 ppm, of lead <=20 ppm, of arsenic <=3 ppm and of mercury <=1 ppm, and 95% of the grain size to be <45 μm.

The composition is advantageously such that the metallic core consists of silver, the content of mercury is <=1 ppm, of arsenic <=5 ppm, of lead <=10 ppm, and the content of silver is >=99.9%, or the metallic core consists of silver and the content of silver is >=99.5%, or the metallic core consists of gold, the content of silver is <=7%, copper <=4%, and the gold content is >=90%.

A layer may advantageously be provided in such a way that the weight ratio of coating to metallic core is between 1 and 0.001.

An inventive pigment may additionally be characterized in that the metallic core is ground with the aid of a plant-based lubricant, especially plant-based oleic acid or stearic acid, and shaped preferably flake-shaped with a diameter of 1 to 100 μm and a mean thickness of 0.05 to 2 μm.

The invention additionally relates to the production of a pigment, which is characterized in that the metallic substrate particles are coated without additional pretreatment in a sol-gel process in alcoholic-aqueous solution by means of hydrolysis and vapor deposition of organic metal oxide prestages and optionally with the use of suitable catalysts.

The invention is also aimed at a cosmetic preparation containing an above-characterized pigment.

The invention will be described in more detail below based on two examples for producing inventive metal effect pigments:

EXAMPLE 1

In a 1-liter round flask provided with reflux condenser and stirring apparatus, 100 g of a gold bronze pigment (mean particle diameter approximately 17 μm) that has been ground with plant-based stearic acid is dispersed in 500 ml ethanol, the mixture is heated to 50° C., and 4.5 g of a 15% aqueous solution of DMEA are added. Over the course of 8 hours, a solution of 17.3 g tetraethoxysilane in 52 g ethanol is dosed in. After completed addition, the mixture is cooled off slowly and stirred for an additional 8 hours at room temperature.

The gold bronze pigment that is coated with $SiO_2$ is separated by filtration, washed with 200 ml ethanol and dried at 80° C. in the vacuum drying chamber.

The obtained product has a $SiO_2$ content of 4.7% and exhibits, after application in a nitrocellulose lacquer, optical properties with high metallic luster that are comparable to the utilized starting material.

EXAMPLE 2

In a 1-liter round flask provided with reflux condenser and stirring apparatus, 75 g of an aluminum pigment (mean particle diameter approximately 23 μm) that has been ground with plant-based oleic acid is dispersed in 600 ml butyl glycol, the mixture is heated to 95° C., and 50 g of a 5% aqueous solution of DMEA are added. Over the course of 12 hours, a solution of 24.7 g tetraethoxysilane in 24.7 g butyl glycol is dosed in. After completed addition, the mixture is cooled off slowly and stirred for an additional 8 hours at room temperature.

The aluminum pigment that is coated with $SiO_2$ is separated by filtration, washed twice with 200 ml ethanol in each case and dried at 100° C. in the vacuum drying chamber.

The obtained product has a $SiO_2$ content of 8.8% and exhibits, after application in a nitrocellulose lacquer, optical properties with high metallic luster that are comparable to the utilized starting material.

To better illustrate the invention, two example embodiments for cosmetic preparations containing inventive pigments will be described below:

EXAMPLE 1

| Creamy eye decoration preparation | |
|---|---|
| Product Description | Wt. % |
| Isopropyl myristate | 23 |
| Magnesium stearate | 2 |
| Mineral oil | 25 |
| Bees wax | 40 |
| $SiO_2$-coated gold bronze pigment (mean particle size 35 μm) | 10 |

The fat mass is heated to approximately 110° C. The melted mass is subsequently allowed to cooled down. Pigment is added to 2 g of the melted mass. A renewed careful melting and stirring follows. The mass that is obtained in this manner, which is not overly hot, is poured into a form.

EXAMPLE 2

| Rouge Powder | |
|---|---|
| Product Description | Wt. % |
| Talcum | 33 |
| Potato starch | 20 |
| Magnesium stearate | 8 |
| Calcium carbonate | 4 |
| $SiO_2$-coated gold bronze pigment (mean particle size: 17 μm) | 19 |
| $SiO_2$-coated copper pigment (mean particle size 17 μm) | 16 |

The components are mixed and homogenized. The mixture is compressed at 40 bar and shaped.

The invention claimed is:

1. A metal pigment for a cosmetic preparation, such as lipstick, nail polish, eye shadow, hair colorant, liquid mascara, powder, eyeliner, rouge, skin/hair care products, perfume, eau de toilette, lotions, characterized in that a metallic substrate has a substrate-enclosing single layer thereover produced by the sol-gel process, which provides a barrier effect against sweat and saliva and prevents direct contact between skin and metallic substrate; and consists of silicon oxide, aluminum oxide, iron oxide, ceroxide, chromium oxide, corresponding hydrates, or mixtures thereof;

said layer having a thickness of between 20 and 50 nm;

said single layer being the only layer over said metallic substrate;

wherein the metallic substrate consists of aluminum, exclusive of impurities, 100% of the grain size is <75 μm and 95% is <45 μm and the content of mercury is <=1 ppm, of arsenic <=3 ppm, of lead <=20 ppm, and the Al content is >=99%.

2. A metal pigment according to claim 1, characterized in that the layer is compatible with a binding agent or carrier of the cosmetic preparation.

3. A pigment according to claim 1, wherein the content of mercury is <=1 ppm, of arsenic <=3 ppm, of lead <=10 ppm, of cadmium <=1 ppm, of heavy metals (as lead) <=40 ppm, the drying loss at 105° C. is <=0.5%, and the Al content is >=99%.

4. A metal pigment in the form of a bronze pigment, for a cosmetic preparation, such as lipstick, nail polish, eye shadow, hair colorant, liquid mascara, powder, eyeliner, rouge, skin/hair care products, perfume, eau de toilette, lotions, characterized in that
   a metallic substrate or core has a single substrate-enclosing layer thereover, produced by the sol-gel process, which provides a baffler effect against sweat and saliva and prevents direct contact between skin and the metallic substrate; and
   consists of silicon oxide, aluminum oxide, iron oxide, ceroxide, chromium oxide, corresponding hydrates, or mixtures thereof;
   said layer having a thickness of between 20 and 50 nm;
   said layer being the only layer over said metallic substrate;
   wherein the metallic core contains a content of copper of 70 to 95%, a content of zinc <=30% and a content of aluminum and tin of <=0.5% in each case, and the content of cadmium is <=15 ppm, of lead <=20 ppm, of arsenic <=3 ppm and of mercury <=1 ppm, and 95% of the grain size is <45 μm.

5. A metal pigment, for a cosmetic preparation, such as lipstick, nail polish, eye shadow, hair colorant, liquid mascara, powder, eyeliner, rouge, skin/hair care products, perfume, eau de toilette, lotions, characterized in that
   a metallic substrate or core has a single substrate-enclosing layer thereover, produced by the sol-gel process, which provides a barrier effect against sweat and saliva and prevents direct contact between skin and the metallic substrate; and
   consists of silicon oxide, aluminum oxide, iron oxide, ceroxide, chromium oxide, corresponding hydrates, or mixtures thereof;
   said layer having a thickness of between 20 and 50 nm;
   said layer being the only layer over said metallic substrate;
   wherein the metallic core consists of silver exclusive of impurities, the content of mercury is <=1 ppm, of arsenic <=5 ppm, of lead <=10 ppm, and the content of silver is >=99.5%.

6. A pigment according to claim 5, wherein the content of silver in the core is >=99.9%.

7. A metal pigment, for a cosmetic preparation, such as lipstick, nail polish, eye shadow, hair colorant, liquid mascara, powder, eyeliner, rouge, skin/hair care products, perfume, eau de toilette, lotions, characterized in that
   a metallic substrate or core has a single substrate-enclosing layer thereover, produced by the sol-gel process, which provides a barrier effect against sweat and saliva and prevents direct contact between skin and the metallic substrate; and
   consists of silicon oxide, aluminum oxide, iron oxide, ceroxide, chromium oxide, corresponding hydrates, or mixtures thereof;
   said layer having a thickness of between 20 and 50 nm;
   said layer being the only layer over said metallic substrate;
   wherein the metallic core consists of, exclusive of incidental impurities, >=90% gold, <=7% silver, and <=4% copper.

8. A pigment according to claim 1, characterized in that the weight ratio of the layer to the metallic core is between 1 and 0.001.

9. A pigment according to claim 1, characterized in that the metallic substrate is a metal pigment produced through grinding with lubricants of plant origin.

10. A pigment according to claim 1, characterized in that the metallic core is formed flake-like with a diameter of 1 to 100 μm and a mean thickness of 0.05 to 2 μm.

11. A method for producing a pigment according to claim 1, characterized in that the metallic substrate particles are coated without additional pretreatment in a sol-gel process in alcoholic-aqueous solution through hydrolysis and vapor depositing of organic metal oxide pre-stages and optionally with the use of suitable catalysts.

12. A cosmetic preparation containing a pigment according to claim 1.

13. A method for producing a pigment according to claim 4, characterized in that the metallic substrate particles are coated without additional pretreatment in a sol-gel process in alcoholic-aqueous solution through hydrolysis and vapor depositing of organic metal oxide pre-stages and optionally with the use of suitable catalysts.

14. A cosmetic preparation containing a pigment according to claim 4.

15. A method for producing a pigment according to claim 5, characterized in that the metallic substrate particles are coated without additional pretreatment in a sol-gel process in alcoholic-aqueous solution through hydrolysis and vapor depositing of organic metal oxide pre-stages and optionally with the use of suitable catalysts.

16. A cosmetic preparation containing a pigment according to claim 5.

17. A method for producing a pigment according to claim 7, characterized in that the metallic substrate particles are coated without additional pretreatment in a sol-gel process in alcoholic-aqueous solution through hydrolysis and vapor depositing of organic metal oxide pre-stages and optionally with the use of suitable catalysts.

18. A cosmetic preparation containing a pigment according to claim 7.

* * * * *